(12) United States Patent
Palti

(10) Patent No.: US 10,780,287 B2
(45) Date of Patent: Sep. 22, 2020

(54) RETROFIT TO PROTECT IMPLANTED DEVICES (E.G., PACEMAKERS) FROM UNAUTHORIZED MANIPULATION

(71) Applicant: Yoram Palti, Haifa (IL)

(72) Inventor: Yoram Palti, Haifa (IL)

(73) Assignee: Terafence Ltd., Haifa (IL)

( * ) Notice: Subject to any disclaimer, the term of this patent is extended or adjusted under 35 U.S.C. 154(b) by 0 days.

(21) Appl. No.: 16/499,287

(22) PCT Filed: Apr. 5, 2018

(86) PCT No.: PCT/IB2018/052367
§ 371 (c)(1),
(2) Date: Sep. 29, 2019

(87) PCT Pub. No.: WO2018/185703
PCT Pub. Date: Oct. 11, 2018

(65) Prior Publication Data
US 2020/0101301 A1     Apr. 2, 2020

Related U.S. Application Data

(60) Provisional application No. 62/482,394, filed on Apr. 6, 2017.

(51) Int. Cl.
*A61N 1/372*  (2006.01)
*A61N 1/362*  (2006.01)
(Continued)

(52) U.S. Cl.
CPC ........... *A61N 1/3931* (2013.01); *A61N 1/362* (2013.01); *A61N 1/37217* (2013.01);
(Continued)

(58) Field of Classification Search
CPC combination set(s) only.
See application file for complete search history.

(56) References Cited

U.S. PATENT DOCUMENTS

2008/0071328 A1   3/2008  Haubrich et al.
2009/0270949 A1   10/2009 Kalpin et al.
(Continued)

OTHER PUBLICATIONS

Written Opinion and International Search Report issued for application No. PCT/IB2018/052367 dated Jun. 20, 2018.

*Primary Examiner* — Paula J Stice
(74) *Attorney, Agent, or Firm* — Potomac Law Group, PLLC

(57) ABSTRACT

An implantable device that (a) has an analog input configured to detect analog electrical signals and (b) is configured to accept RF commands can be retrofitted to prevent unauthorized access by modifying the software of the implantable device to (1) accept control commands that arrive via the analog input and (2) ignore control commands that arrive via the RF transceiver. Ultrasound communications can then be detected and inductively coupled onto a lead that is connected to the analog input. In some embodiments, the modified implantable device can only be controlled via ultrasound signals at all times to improve security. In other embodiments, the modified implantable device can only be controlled via non-ultrasound signals (e.g., RF signals) for short periods of time after the system has been unlocked in response to receipt of a specific ultrasound signal.

20 Claims, 10 Drawing Sheets

(51) Int. Cl.
*A61N 1/39* (2006.01)
*A61N 1/40* (2006.01)
*H04W 12/08* (2009.01)

(52) U.S. Cl.
CPC ....... *A61N 1/37254* (2017.08); *A61N 1/3956* (2013.01); *A61N 1/40* (2013.01); *H04W 12/0808* (2019.01)

(56) References Cited

U.S. PATENT DOCUMENTS

| | | | |
|---|---|---|---|
| 2012/0215285 A1* | 8/2012 | Tahmasian | H04B 5/0037 607/59 |
| 2016/0250486 A1* | 9/2016 | Yoder | G16H 40/63 340/870.07 |
| 2018/0150624 A1 | 5/2018 | Palti | |
| 2019/0240495 A1 | 8/2019 | Palti et al. | |

* cited by examiner

RETROFIT TO PROTECT IMPLANTED DEVICES (E.G., PACEMAKERS) FROM UNAUTHORIZED MANIPULATION

CROSS REFERENCE TO RELATED APPLICATIONS

This Application claims the benefit of U.S. Provisional Application 62/482,394 filed Apr. 6, 2017, which is incorporated herein by reference in its entirety.

BACKGROUND

Implanted devices (also referred to herein as implants) such as pacemakers and Implantable Cardioverter Defibrillators (ICDs) usually function autonomously. But from time to time their operation may have to be controlled. In the case of pacemakers, for example, this control can be used to adjust the pacing rate or stimulating pulse characteristics, or in CRT pacers for resynchronization of pacing of the different cardiac chambers, etc.

Conventional implanted devices can typically be controlled by RF signals that are transmitted from outside the user's body to the device. One drawback of this conventional hardware configuration and communication protocol is that it is susceptible to being accidently affected by spurious RE (e.g., from airport security gates) and is also susceptible to being manipulated or hacked by unauthorized entities. These activities could pose danger to the wellbeing of the person using the implant or wearable device, and in certain circumstances could even he life-threatening. The situation is compounded because conventional implanted devices typically can be accessed using standard communication protocols (e.g., Bluetooth™) that are well known to the public.

SUMMARY OF THE INVENTION

One aspect of the invention is directed to a system for implementing secure communication with an implanted device. The system comprises an implantable apparatus and an auxiliary apparatus. The implantable apparatus includes (1) an implantable device configured for implantation into a body, the implantable device having an RE transceiver and a first input configured to detect analog electrical signals, wherein the implantable device has been modified by a software update from an original state in which the implantable device is configured to accept control commands that arrive via the RF transceiver to an updated state in which the implantable device is configured to accept control commands that arrive via the first input and ignore control commands that arrive via the RF transceiver, (2) a coil that is inductively coupled with a lead connected to the first input of the implantable device, (3) a coil driver circuit configured to energize the coil in response to application of control signals, (4) a first ultrasound transducer that generates a first electrical output signal in response to a first incoming ultrasound signal, (5) a first ultrasound frequency receiver that generates, based on the first electrical output signal, first data corresponding to commands that have been encoded onto the first incoming ultrasound signal, and (6) a first controller configured to generate the control signals based on the first data, wherein the control signals are routed to the coil driver circuit. The control signals generated by the first controller are configured to cause the coil driver circuit to energize the coil so as to induce, onto the lead, analog signals that correspond to the control commands that arrive via the first input of the implantable device. The auxiliary apparatus includes a second controller configured to generate commands for controlling the implantable device, a first ultrasound frequency transmitter that encodes the commands generated by the second controller onto a first driving signal, and a second ultrasound transducer that generates a second ultrasound output signal in response to the first driving signal.

Another aspect of the invention is directed to an implantable apparatus that comprises an implantable device configured for implantation into a body. The implantable device has an RF transceiver and a first input configured to detect analog electrical signals, and the implantable device has been modified by a software update from an original state in which the implantable device is configured to accept control commands that arrive via the RF transceiver to an updated state in which the implantable device is configured to accept control commands that arrive via the first input and ignore control commands that arrive via the RF transceiver. The implantable apparatus also comprises a coil that is inductively coupled with a lead connected to the first input of the implantable device, and a coil driver circuit configured to energize the coil in response to application of control signals. The implantable apparatus also comprises a first ultrasound transducer that generates a first electrical output signal in response to a first incoming ultrasound signal. The implantable apparatus also comprises a first ultrasound frequency receiver that generates, based on the first electrical output signal, first data corresponding to commands that have, been encoded onto the first incoming ultrasound signal. The implantable apparatus also comprises a first controller configured to generate the control signals based on the first data, and the control signals are routed to the coil driver circuit. The control signals generated by the first controller are configured to cause the coil driver circuit to energize the coil so as to induce, onto the lead, analog signals that correspond to the control commands that arrive via the first input of the implantable device.

In some embodiments of the implantable apparatus, in the updated state, the implantable device is configured to keep the RF transceiver disabled at all times. In some of these embodiments, the implantable device is configured to keep the RF transceiver disabled at all times by activating hardware that disconnects an RF input of the implantable device. In some of these embodiments, the implantable device is configured to keep the RF transceiver disabled at all times by deactivating software routines that interface with the RF transceiver.

In some embodiments of the implantable apparatus, in the updated state, the implantable device is configured to temporarily enable the RF transceiver in response to a first specific control command that arrives via the first input, and to keep the RF transceiver disabled at all other times. In some of these embodiments, the implantable device is configured to terminate the temporary enablement of the RF transceiver in response to a second specific control command. In some of these embodiments, the implantable device is configured to terminate the temporary enablement of the RF transceiver automatically after a period of time has elapsed.

In some embodiments of the implantable apparatus, the implantable device comprises a pacemaker, and the control commands that arrive via the first input control the pacemaker. In some embodiments of the implantable apparatus, the implantable device comprises an implantable cardioverter defibrillator, and the control commands that arrive via the first input control the implantable cardioverter defibrillator. In some embodiments of the implantable apparatus, the analog electrical signals have an amplitude of less than 5 mV.

Another aspect of the invention is directed to a method of retrofitting an implantable device to provide secure communications. This method comprises obtaining an implantable device configured for implantation into a body. The implantable device has an RF transceiver and a first input configured to detect analog electrical signals, and the implantable device is configured to accept control commands that arrive via the RF transceiver. This method also comprises modifying software of the implantable device to an updated state in which the implantable device is configured to accept control commands that arrive via the first input and ignore control commands that arrive via the RF transceiver. This method also comprises inductively coupling a coil to a lead connected to the first input of the implantable device, and energizing the coil in response to application of control signals. This method also comprises generating a first electrical output signal in response to a first incoming ultrasound signal. This method also comprises generating, based on the first electrical output signal, first data corresponding to commands that have been encoded onto the first incoming ultrasound signal. This method also comprises generating the control signals based on the first data. The control signals are configured to energize the coil so as to induce, onto the lead, analog signals that correspond to the control commands that arrive via the first input of the implantable device.

In some embodiments of the method, in the updated state, the implantable device is configured to keep the RF transceiver disabled at all times. In some of these embodiments, the implantable device is configured to keep the RF transceiver disabled at all times by activating hardware that disconnects an RF input of the implantable device. In some of these embodiments, the implantable device is configured to keep the RF transceiver disabled at all times by deactivating software routines that interface with the RF transceiver.

In some embodiments of the method, in the updated state, the implantable device is configured to temporarily enable the RF transceiver in response to a first specific control command that arrives via the first input, and to keep the RF transceiver disabled at all other times. In some of these embodiments, the implantable device is configured to terminate the temporary enablement of the RF transceiver in response to a second specific control command. In some of these embodiments, the implantable device is configured to terminate the temporary enablement of the RF transceiver automatically after a period of time has elapsed.

In some embodiments of the method, the implantable device comprises a pacemaker, and the control commands that arrive via the first input control the pacemaker. In some embodiments of the method, the implantable device comprises an implantable cardioverter defibrillator, and the control commands that arrive via the first input control the implantable cardioverter defibrillator.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
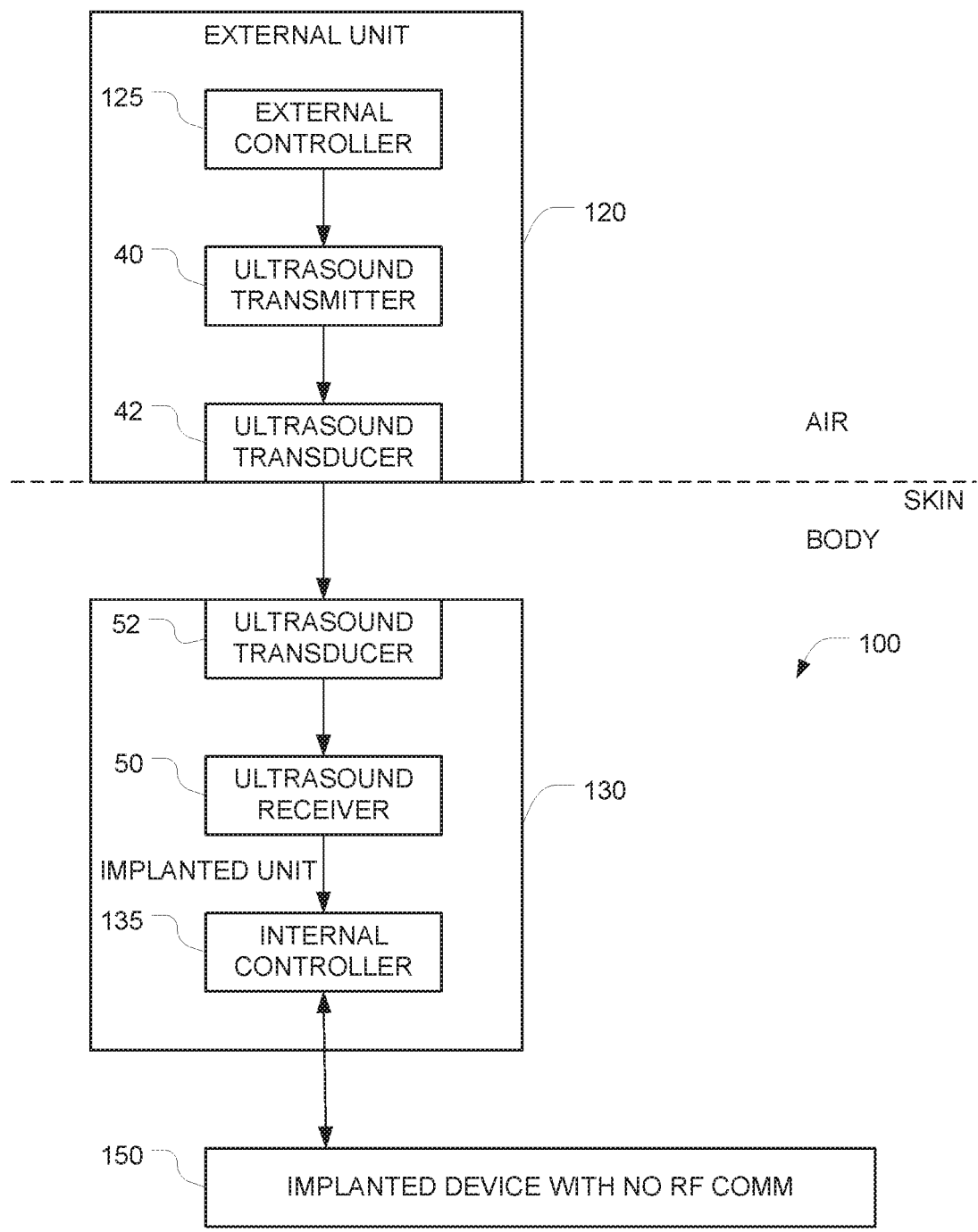
FIG. 1 depicts an example of a system for implementing secure ultrasound communication with an implanted device.

The embodiments described herein protect implanted from being accidently affected, manipulated, or hacked by unauthorized entities. In some embodiments, the implanted device has been previously deployed, and is retrofitted as described herein to incorporate additional protection features.

This application relates to the available ability to remotely control implanted devices that have an electrical sensing function including but not limited to pacemakers and Implantable Cardioverter Defibrillators (ICDs). The embodiments described herein overcome the dangers noted above by ensuring that the only way to access and control the implant is by mechanical waves such as ultrasound. In the case of medical implants because the mechanical impedance of the human body is very different from that of the ambient air, there is an impedance mismatch that prevents the penetration of the pressure waves from the air into the body, thus protecting it from remote interference with the implant function. Thus, to control an implanted ultrasound activated device, in practice, one has to make contact with the body. In most situations, this will be very difficult for a hacker or terrorist to accomplish.

To maximize the power transfer or minimize signal reflection from the load there should be an impedance match. For example, the mechanical impedance of air to MHz range ultrasound waves is $4 \times 10^2$ (kg/m$^2$-sec) while that of water is $1.5 \times 10^6$. This fact results in transmission of only 0.1% of the energy across the interface. Similarly, for example, the impedance of muscle and fat are very similar and close to that of water: $1.7 \times 10^6$ and $1.3 \times 10^6$ (kg/m$^2$-sec) correspondingly, and therefore the transmission across the soft tissue/water interface is 99.77%. Note that the impedance of metals, aluminum for example is $17 \times 10^6$ (kg/m$^2$-sec), i.e. fairly close to that of human tissue, and very different from air. Thus, metal enclosed devices with ultrasound sensors are well protected from both air-born ultrasound and RF waves.

In view of the above, the only practical way to control an implant using an ultrasound signal is to position an ultrasound transducer in firm contact (preferably with intervening gel) with the 'skin of the person who has the implant. The embodiments described below take advantage of this situation by designing the system so that either (a) the system can only be controlled via ultrasound signals, or (b) the system can only be controlled via non-ultrasound signals (e.g., RF) after the system has been unlocked in response to receipt of a particular ultrasound signal.

In a first example of a secure communication system using ultrasound, a device is implanted in a living body (which is similar in its mechanical wave conduction and impedance properties to water) where communication can be achieved only by direct contact.

Note that the impedance matching level of protection described herein may be used as the only security mechanism, or in alternative embodiments it may be used in addition to additional security measures (e.g., encryption, etc.).

FIG. 1 depicts an example of a system for implementing secure communication with an implantable device 150 that has been implanted into a body (e.g., a human body). In this example, the implantable device 150 can only be controlled via ultrasound signals, and it is impossible to control the implantable device 150 using RF signals.

The system includes an implantable apparatus 100 and an external unit 120 (also referred to herein as an auxiliary apparatus). The implantable apparatus 100 includes the implantable device 150 and additional implanted components 130, both of which are configured for implantation into a body. Examples of devices that can be implanted include, but are not limited to, pacemakers and ICDs. The implantable device 150 has at least one control input, and the implantable device 150 is controlled by the additional implanted components 130 via at least one electrical control signal that is applied to the at least one control input. The implantable apparatus 100 is configured to ignore all attempts to control the implantable device 150 via RF signals. This may be accomplished, for example, by starting with a conventional implanted device (e.g., a pacemaker) that is controllable via RF signals, and disabling the RF section of the device either in software (e.g., firmware), in hardware (e.g. by grounding a control line), or by surrounding the implanted device by suitable shielding that prevents RF energy from reaching the implanted device. Alternatively, this may be accomplished by omitting the RF circuitry entirely from the implanted device.

Because it is impossible to control the implantable device 150 via RF, an alternative signal path must be provided in order to obtain control of the implantable device 150. As noted above, the implantable device 150 has at least one hardwired control input, and the implantable device is controllable by applying at least one electrical control signal to the at least one hardwired control input. And it is this at least one hardwired control input that is used to control the implantable device 150. Note that the software and or hardware of the implantable device 150 must be configured to respond to commands that arc received via this at least one hardwired control input.

In the FIG. 1 embodiment, the alternative signal path that is used to control the implantable device 150 comprises the additional implanted components 130. In the illustrated example, these additional implanted components 130 comprise a first ultrasound transducer 52, a first ultrasound frequency receiver 50, and a first controller 135 (also referred to herein as an internal controller). These additional implanted components 130 may be housed in a housing that is separate from the housing of the implantable device 150. In alternative embodiments, the implantable device 150 and the additional implanted components 130 may be housed together in a single housing.

The external unit 120, which is positioned outside the body controls the implantable device 150 by coupling ultrasound waves into the body so that those ultrasound waves can travel through the body and arrive at the implanted apparatus 100. After they reach the implanted apparatus 100, the ultrasound waves are converted to an electrical signal by the ultrasound transducer 52, and that electrical signal is received by the ultrasound receiver 50. The output of the ultrasound receiver 50 is provided to an internal controller 135 which, in turn, generates hardwired control signals that are provided to the implantable device 150. The external unit 120 is preferably housed in an appropriate housing that makes it possible to bring the ultrasound transducer 42 into contact with the surface of the body (e.g., the surface of the subject's skin). This ultrasound transducer 42 is driven by an ultrasound transmitter 40 which, in turn, is controlled by the external controller 125 within the external unit 120.

The first ultrasound transducer 52 is positioned with respect to the housing so that incoming ultrasound signals traveling through the body will arrive at the first ultrasound transducer 52. The first ultrasound transducer 52 generates a first electrical output signal in response to these first incoming ultrasound signals. The first ultrasound frequency receiver 50 generates, based on the first electrical output signal, first data corresponding to commands that have been encoded onto the first incoming ultrasound signal. The ultrasound receiver 50 includes whatever components are necessary to extract the first data that is encoded in the first electrical output signal that it receives. Examples include amplification, signal shaping, demodulation, analog to digital conversion, and other functions that will be apparent to persons skilled in the relevant arts.

The ultrasound receiver 50 outputs the first data to the first controller 135. The first controller 135 is configured to (a) generate, based on the first data, the at least one electrical control signal, and (b) to apply the generated at least one electrical control signalto the at least one control input of the implantable device 150. The implantable device 150 will then respond to those commands.

The auxiliary apparatus 120 includes a second controller 125 (also referred to herein as an external controller) configured to generate commands for controlling the implantable device 150. Control of the auxiliary apparatus 120 may be effectuated using any appropriate user interface, the details of which will be apparent to persons skilled in the relevant arts. The auxiliary apparatus 120 also includes a first ultrasound frequency transmitter 40 that encodes the commands generated by the second controller onto a first driving signal, and a second ultrasound transducer that generates a second ultrasound output signal in response to the first driving signal. It is this second ultrasound output signal that is transmitted into the body (e.g. into the subject's body).

When the auxiliary apparatus 120 is placed against the surface of the body (e.g., against a human subject skin) so that the ultrasound transducer 42 is in acoustic contact with the surface of the body, the auxiliary apparatus 120 can transmit commands into the body via ultrasound. Optionally, ultrasound gel (e.g., similar to the gels used for medical sonograms) may be used to enhance the acoustic coupling between the ultrasound transducer 42 and the surface of the body, The signal path from the external controller 125 to the internal controller 135 includes an ultrasound frequency transmitter 40 and an ultrasound frequency receiver 50. Although the exact nature of the transmitter 40 and the receiver 50 is not critical, the receiver 50 should be designed to be the counterpart of the transmitter 40. For example, if the transmitter 40 uses a particular approach to encode the commands that it receives from the second controller 125, the receiver 50 should use the counterpart of that approach to decode the electrical signals that it receives. Examples of suitable approaches for encoding and decoding include digital modulations/demodulation techniques (including but not limited to amplitude-shift keying, phase-shift keying, pulse-position modulation, etc.) and analog modulation/demodulation techniques (including but not limited to amplitude modulation, frequency modulation, phase modulation, etc.). Optionally, differential pulse position modulation may be used for implementing synchronization. In some embodiments, the external controller 125 implements framing of the data prior to transmission. In some embodiments, the external controller 125 encodes the data prior to transmission in the ultrasound pulse intervals and/or durations, and/or position, etc.

Depending on the nature of the modulation/encoding scheme, responsibility for portions of the encoding process may be shifted out of the transmitter 40 and into the external controller 125. Similarly, responsibility for portions of the decoding process may be shifted out of the receiver 50 and into the internal controller 135.

Any suitable communication protocol may be used. For example, the message, data, or command may be determined by the specific protocol. Optionally, the internal controller 135 may be configured to check all incoming data for integrity using any of a variety of techniques. The protocol may also implement an error detection or error correction logic (e.g. simple parity, checksums, to more complex Hanning code, or other). This can help the receiver side to understand if the message/command/data detected is valid or might be corrupted.

Optionally, a secure communication protocol may be employed by the system e.g., by having the external controller 125 encrypt the data that it sends to the ultrasound transmitter 40 and by having the internal controller 135 decrypt the data that it receives from the ultrasound receiver 50. A wide variety of approaches for implementing this encryption/decryption or another security protocol can be used, the details of which will be apparent to persons skilled in the relevant arts.

To improve coupling between the external unit 120 and the implantable apparatus 100, an ultrasound gel may be interposed between the external unit 120 and the surface of the body (e.g. surface of the subject skin). In addition, the external unit 120 may be positioned so that the ultrasound transducer 42 touches the surface of the body at a location that is close to the location of the implantable apparatus 100. When the implantable apparatus 100 is implanted within a subject's body), the ultrasound transducer 52 is preferably positioned to make contact with tissue within the subject's body.

Notably, whenever the auxiliary apparatus 120 is not touching the surface of the body (e.g. the surface of the skin of a human body) and is not in acoustic contact with the surface of the body, the auxiliary apparatus 120 will not be able to send its commands into the body via ultrasound. This renders the implantable device 150 immune from external control.

One potential drawback of the FIG. 1 embodiment is that, due to the one-way data path, the external controller 125 has no way of verifying if a command that it issued has actually arrived at the internal controller 135. One way to minimize this potential drawback is to have software in the internal controller 135 take into account a possible mistake in the sending of information from the external unit 120 to the implantable device 150.

Figure 2:
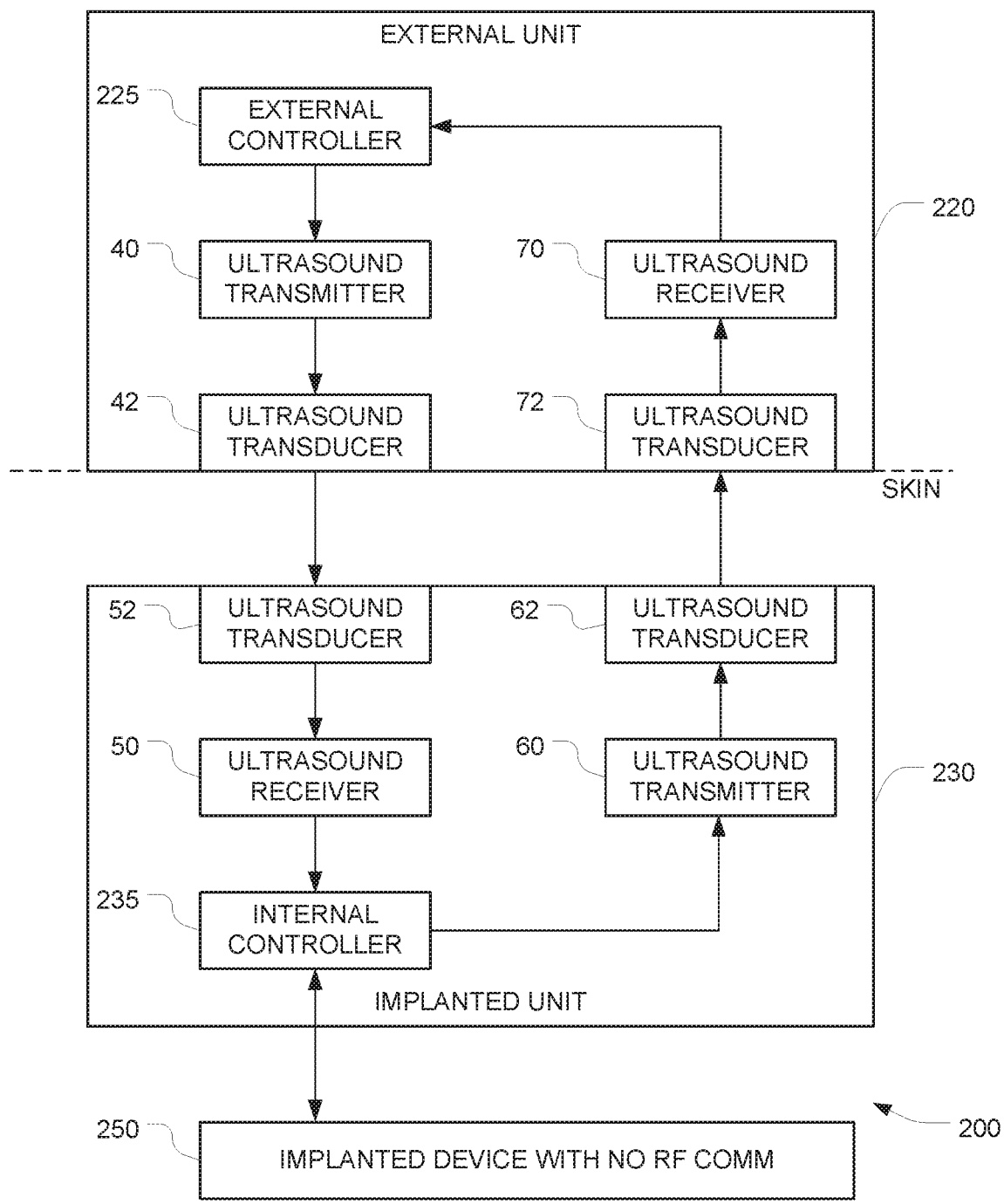
FIG. 2 depicts an example of a system for implementing secure ultrasound communication with an implanted device with an additional ultrasound data path in the opposite direction.

FIG. 2 depicts a way to overcome this potential drawback entirely by adding additional components to the FIG. 1 embodiment. In FIG. 2, the data path from the external controller 225 in the external unit 220 to the internal controller 235 in the additional implanted components 230 and into the implantable device 250 is similar to the data path from the external controller 125 to the internal controller 135 and the implantable device 150, as described above in connection with FIG. 1, And the implantable device 250 is similar to the implantable device 150 in the FIG. 1 embodiment. But in the FIG. 2 embodiment, an additional data path in the opposite direction (i.e. from the internal controller 235 to the external controller 225) is provided. This additional data path can be used to verify receipt of commands and to report status of the implantable device 250.

The operation of the internal controller 235 is similar to the operation of the internal controller 135 in the FIG. 1 embodiment, except that the internal controller 235 is configured to also send data in the reverse direction (i.e. towards the external controller 225) and that the external controller 225 is configured to receive that data. This may be accomplished by configuring the internal controller 235 to generate second data that is indicative of receipt of the first data.

In some of these embodiments, the logical loop of communication is "terminated" by one or more communication channels that enable the implantable device 250 to echo back to the external unit 220 information about the received data (i.e., the data that arrived at the internal controller 235). The external controller 225 can then check the echoed data and confirm (e.g., using one or more special commands) that indeed the received command was the right one, and the implantable device 250 can continue and use this command/data/message, The implantable apparatus 200 in this embodiment has a second ultrasound frequency transmitter 60 that encodes the second data onto a second driving signal, and a third ultrasound transducer 62 that generates a third ultrasound output signal in response to the second driving signal. The third ultrasound output signal has frequency and amplitude characteristics that permit the third ultrasound output signal to reach an external surface of the body (e.g, the subject's skin). Note that while FIG. 2 depicts the first ultrasound transducer 52 and the third ultrasound transducer 62 as separate blocks, a single physical ultrasound transducer may serve as both the first ultrasound transducer 52 and the third ultrasound transducer 62.

The auxiliary apparatus 220 has a fourth ultrasound transducer 72 arranged to detect the third ultrasound output signal when the fourth ultrasound transducer 72 is placed in acoustic contact with a surface of the body, and to generate a fourth electrical output signal that corresponds to the third ultrasound output signal. Note that while FIG. 2 depicts the second ultrasound transducer 42 and the fourth ultrasound transducer 72 as separate blocks, a single physical ultrasound transducer may serve as both the second ultrasound transducer 42 and the fourth ultrasound transducer 72.

The auxiliary apparatus 220 also includes a second ultrasound frequency receiver 70 that generates, based on the fourth electrical output signal, fourth data. This fourth data is provided to the second controller, and the fourth data has some correspondence to the second data so that when the external controller 225 receives the fourth data, the external controller 225 will know that the internal controller 235 has received the first data.

Figure 3:
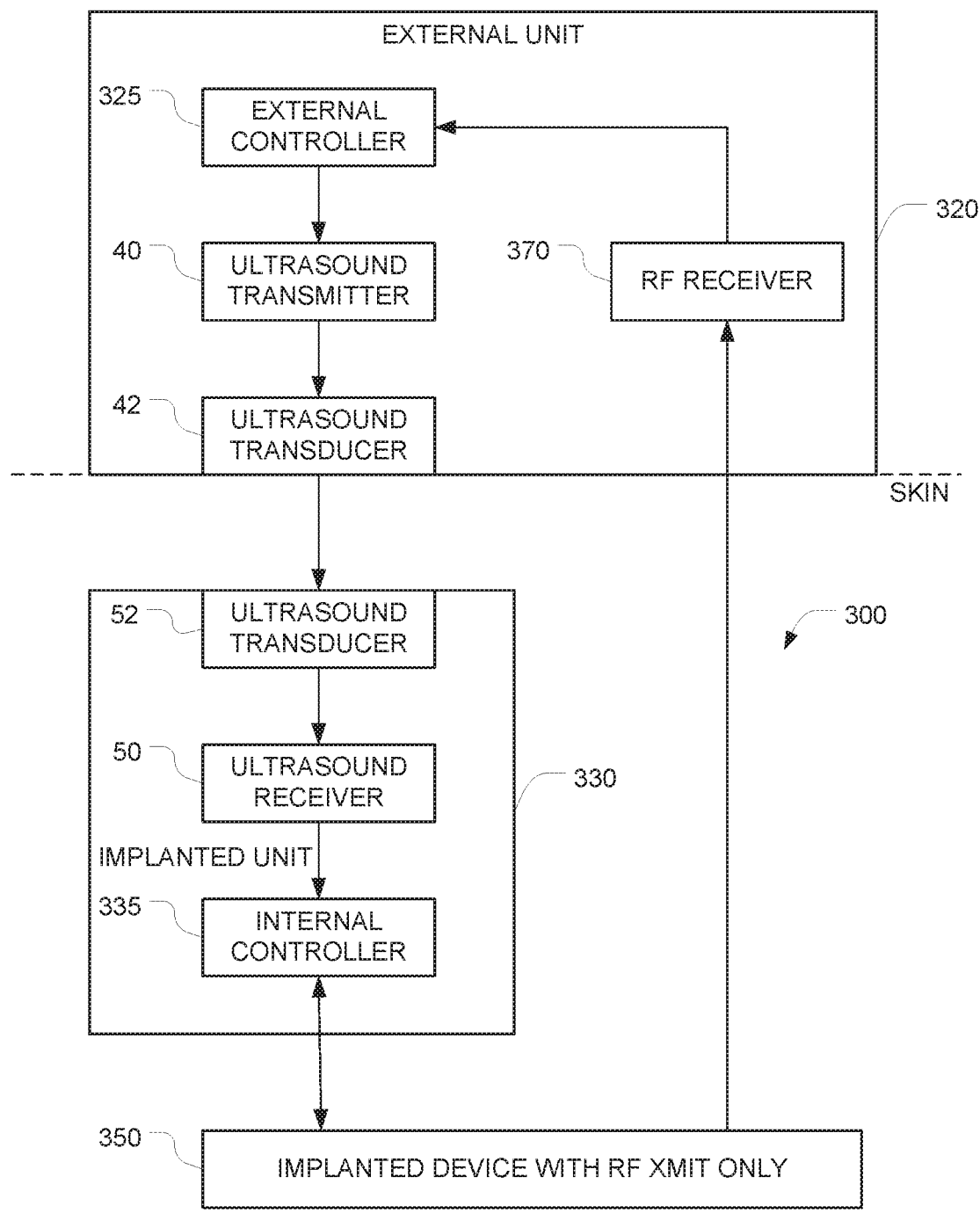
FIG. 3 depicts an example of a system for implementing secure ultrasound communication with an implanted device with an additional RF data path in the opposite direction.

FIG. 3 depicts another embodiment that adds additional components to the FIG. 1 embodiment to overcome the potential drawback noted above. In the FIG. 3 embodiment, the auxiliary apparatus 320 further includes an RF receiver 370, and the implantable apparatus 350 includes an RF transmitter capable of communicating with the RF receiver 370.

In FIG. 3, the data path from the external controller 325 in the external unit 320 to the internal controller 335 in the internal unit 330 and into the implantable device 350 is similar to the data path from the external controller 125 to the internal controller 135 and the implantable device 150, as described above in connection with FIG. 1. And the implantable device 350 is similar to the implantable device 150 in the FIG. 1 embodiment. But in the FIG. 3 embodiment, an additional data path in the opposite direction (i.e. from the implantable device 350 to the external controller 225) is also provided. This additional data path can be used to verify receipt of commands and to report status of the implantable device 350.

The operation of the internal controller 335 is similar to the operation of the internal controller 135 in the FIG. 1 embodiment. Here, the implantable device 350 has an RF transmitter, and that RF transmitter is configured to send data in the reverse direction (i.e. towards the external controller 325) and that the external controller 325 is configured to receive that data. This may be accomplished by configuring the implantable device 350 to generate return data that is indicative of receipt of the first data. Notably, the implantable device 350 does not have the ability to receive data via RF (e.g, because it has no corresponding hardware to perform that function or because the relevant hardware is disabled). As a result, it will be impossible to control the implantable device 350 by beaming commands into the implantable device 350 via RF.

One example of signal flow for using the FIG. 3 embodiment is as follows. In this discussion, we assume that a user (e.g., a doctor or family member or the person with the implant—someone close and authorized by definition) is using the external unit 320. When the external unit 320 is close (e.g., within RF range) to the implant, the external unit 320 can receive RF communication from the implantable device 350—as it is done in conventional RF communication implants like pacemakers. The user can configure and control the external unit 320 via a keyboard or touch screen or buttons embedded the external unit 320. The external unit 320 software (which runs on the external controller 325) can process authentication of the user—as any normal authentication that any computer software can implement. The user can direct the external unit 320 to present data received from the implant via RF communication. The user can direct the external unit 320 to configure/program/send data to the implant by using the external unit 320 user interface.

The external unit 320 can send data to the implantable device 350 via the ultrasound data link only if the external unit 320 is touching the body (with no air gap between the external unit 320 and the body). If an air gap exists between the external unit 320 and the body, the information from the external unit 320 will not be able to get to its destination i.e., the implant), due to the absence of a communication link.

In some embodiments, the external controller 325 and the implantable device 350 are programmed to authenticate the message sent to the implantable device 350 and feedback the received command or data received via the ultrasound data channel back to the external controller 325 (via the RF channel), and request the user to approve (double check) the command that was sent to the implantable device 350. In some embodiments, the internal controller 335 may be programmed to accept the configuration data (as was sent before) only after it receives a second confirmation command from the user (i.e., the confirmation command, which is also sent via the ultrasound data path).

Any data from the external unit 320 can be sent to the unsecure internet by communication over a suitably programmed secure one-way-only communication link. It is true that the direct RF communication from the implant can be received by any RF receiver device positioned near the body/implant. However, this is not considered a security concern, because in the FIG. 3 embodiment, it is read only information. More specifically, in the FIG. 3 embodiment, it will not be possible to write to the implantable device 350 via RF communication as the implantable device 350 does not have a RF receiver. In these embodiments, the RF hardware is configured so that the external unit 320 has only a RF receiver 370 and the implantable device 350 has only a RF transmitter (this configuration makes transmission from the outside world into the implant impossible). In these embodiments, it will not be possible to write to the external unit 320 from the network, as all communication from the external unit 320 to the unsecured internet will be done via the secure one-way-only device.

Figure 4:
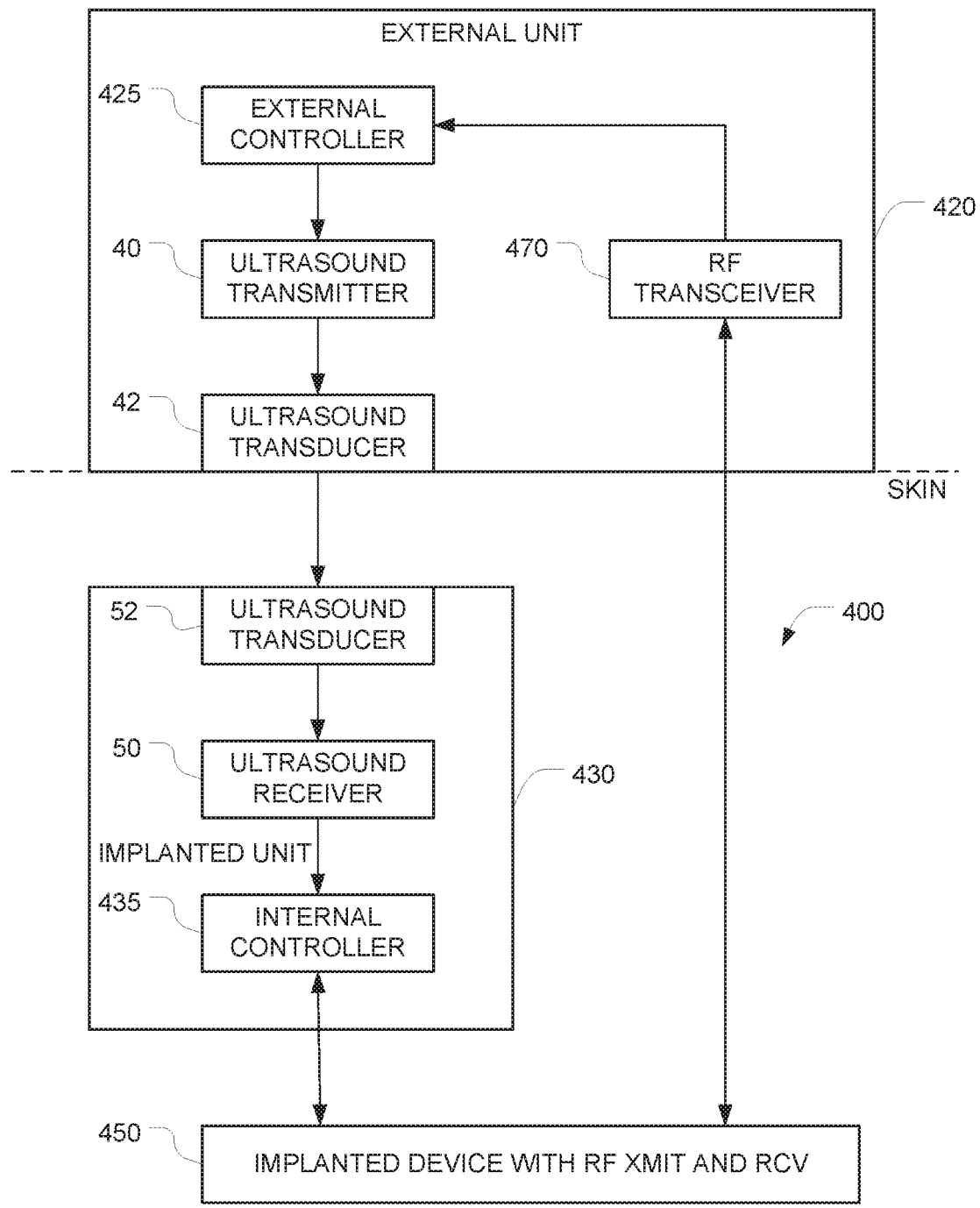
FIG. 4 depicts an example of a system for implementing secure communication with an implanted device using signals that arrive via RF, but only after communications have been enabled using an ultrasound signal.

FIG. 4 depicts an example of a system for implementing secure communication with an implantable device 450 that has been implanted into a body (e.g., a human body). In this embodiment, it is possible to control the implantable device 450 using signals that arrive via RF, but only under certain circumstances. More specifically, in its default state, the implanted system is programmed to ignore all commands that arrive via RF. But the ability to accept commands that arrive via RF can be turned on by sending an appropriate command to the implanted unit via an ultrasound data path. Once RF communication is turned on, communication with the implantable device 450 can proceed in a conventional manner. After a single communication session has ended (e.g. after a predetermined time has elapsed or after an "end session" command is received), the implanted system reverts to its default state in which it will no longer accept commands via RF.

The system includes an implantable apparatus 400 and an external unit 420 (also referred to herein as an auxiliary apparatus). The implantable apparatus 400 includes the implantable device 450 and additional implanted components 430, both of which are configured for implantation into a body. Examples of devices that can be implanted are similar to those described above in connection with FIG. 1 The implantable device 450 has at least one control input, and the implantable device is controllable by applying at least one electrical control signal to the at least one control input. The implantable apparatus 400 is configured so that in its default state, it ignores all attempts to control the implantable device 450 via RF signals. This may be accomplished, for example, by starting with a conventional implantable device (e.g., a pacemaker) that is controllable via RF signals, and disabling the RF section of the device under software control.

The implantable device 450 has an RF transceiver and at least one hardwired control input, and the implantable device is controllable by applying at least one electrical control signal to the at least one hardwired control input. And it is this at least one hardwired control input that is used to switch the implantable device 450 from its default state (in which it ignores RF commands) to an "RF communication enabled" state. Note that the software and or hardware of the implantable device 450 must he configured to respond to commands that are received via this at least one hardwired control input.

In the FIG. 4 embodiment, the signal path that is used to control the state of the implantable device 450 comprises the additional implanted components 430. In the illustrated example, these additional implanted components 430 comprise a first ultrasound transducer 52, a first ultrasound frequency receiver 50, and a first controller 435 (also referred to herein as an internal controller). These additional implanted components 430 may be housed in a housing that is separate from the housing of the implantable device 450. In alternative embodiments, the implantable device 450 and the additional implanted components 430 may be housed together in a single housing.

Operation of the first ultrasound transducer 52 and the first ultrasound frequency receiver 50 is similar to the operation of the corresponding elements in FIG. 1, as described above. The ultrasound receiver 50 outputs first data corresponding to commands that have been encoded onto the first incoming ultrasound signal. This first data is provided to the first controller 435. The first controller 435 is configured to (a) generate, based on the first data, the at least one electrical control signal, and (b) to apply the generated at least one electrical control signal to the at least one control input of the implantable device 450. The implantable device 450 is configured to keep its RF transceiver disabled until the at least one electrical control signal generated by the first controller 435 includes an enable command, and to temporarily enable its RF transceiver after the at least one electrical control signal generated by the first controller 435 includes an enable command.

Based on the description of the implantable apparatus 400 above, it will be apparent that in order to control the implantable apparatus 400, a pathway must be provided for delivering ultrasound signals to the ultrasound transducer 52 in the implantable apparatus 400. In the FIG. 4 embodiment, this is accomplished by the auxiliary apparatus 420, which remains outside of the body.

The operation of the auxiliary apparatus 420 is similar to the operation of the auxiliary apparatus 120 described above in connection with FIG. 1, except that instead of using the external controller to directly control the operation of the implantable device 450, the external controller sends an enable command to the implantable device 450 via a data path that is similar to the data path described above in connection with FIG. 1. Once this enable command is received by the implantable device 450, the implantable device 450 will switch from its default state (in which it ignores commands that arrive via RF) to its "RF communication enabled" state.

The signal path from the external controller 425 to the internal controller 435 is similar to the path between the external controller 125 and the internal controller 135 described above in connection with FIG. 1. And as in FIG. 1, whenever the auxiliary apparatus 420 is not touching the surface of the body (e.g., the surface of a person's skin) and is not in acoustic contact with the surface of the body, the auxiliary apparatus 420 will not be able to send its commands into the body via ultrasound. This renders the implantable device 450 immune from external control.

In this FIG. 4 embodiment, once communication is set up between the external unit 420 and the implantable device 450, subsequent communications between the RF transmitter and the RF receiver may be enabled for a preset duration of time. This alternative may be advantageous because RF communications can be implemented using conventional hardware, and can achieve higher data rates than ultrasound communications. In alternative embodiments for implementing two-way communication, the RF transceiver 470 may be replaced with a RF transmitter and a separate RF receiver.

Figure 5:
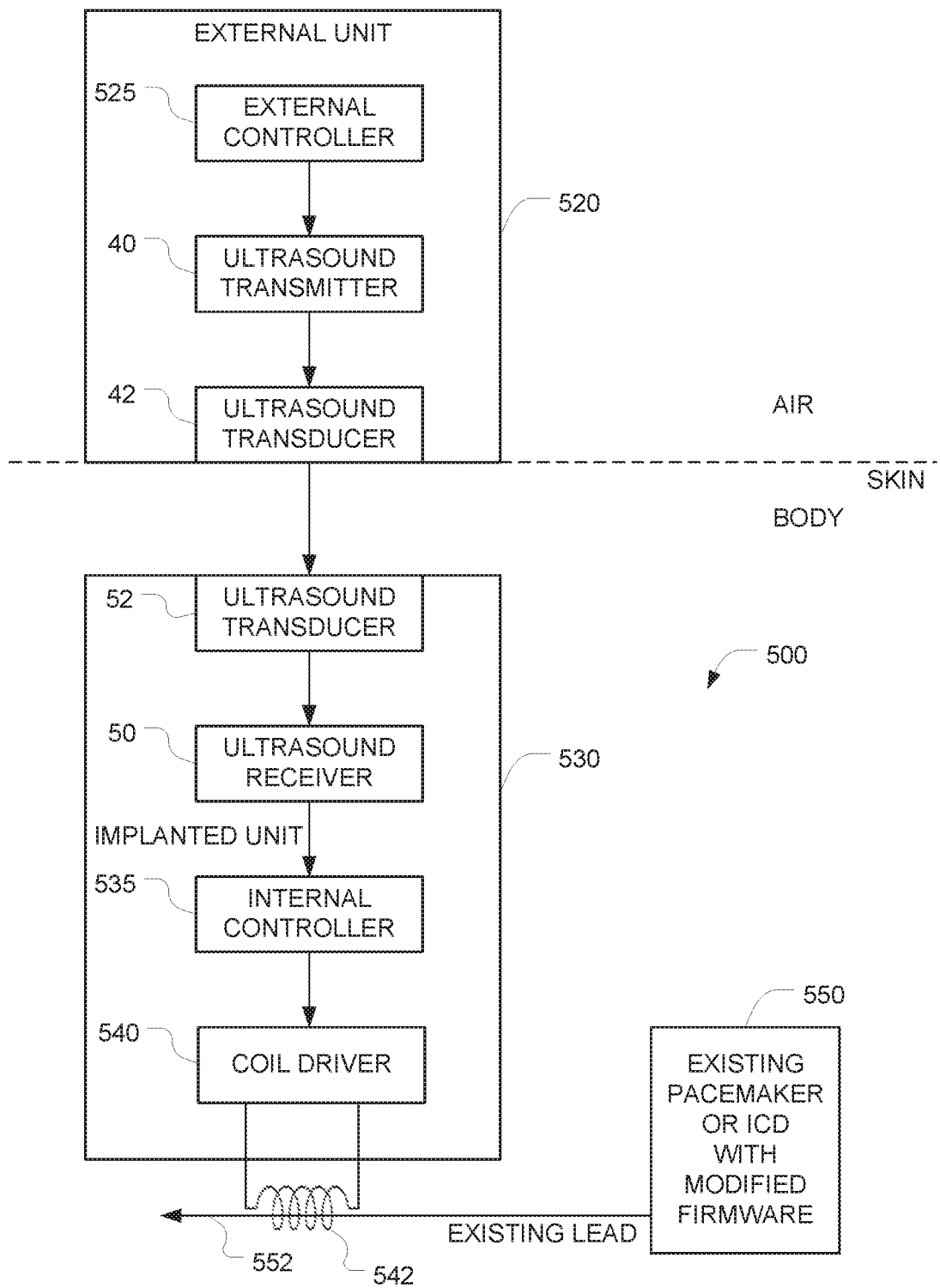
FIG. 5 is a schematic diagram of a system that retrofits protection to a previously implanted implant.

FIG. 5 is a schematic diagram of a system that overcomes the disadvantages of the prior art by retrofitting protection to a previously implanted implant (e.g., a cardiac pacemaker or ICD). We assume that a conventional implant 550 and an associated lead 552 has already been implanted into the patient's body. We also assume that the implant 550 already has a built in control system that permits external control of a variety of the implant's functions. For example, in the context of a pacemaker, the stimulating pulse amplitude and rate, the interval between the various stimuli applied to different cardiac chambers, etc., can all be controlled by sending control signals (e.g., RF control signals) into the pacemaker. We also assume that the software (e.g., firmware) of the implant 550 can be updated.

Additional implanted components 530 are implanted into the patient's body to establish a new communication path with the implant 550. These additional implanted components 530 include an ultrasound transducer 52, an ultrasound receiver 50, and an internal controller 535, the operation of which are similar to the corresponding components described above in connection with FIG. 1. But instead of having the internal controller interface with the implanted device via a hardwired input (as in the FIG. 1 embodiment), an EM coil 542 is implanted into the patient's body at a position where it can interact with the existing lead 552 that is used by the pacemaker 550 to provide pacing and monitor electrical activity of the heart. (For example, the coil may he wrapped around the lead 552.) The internal controller 535 then communicates with the implant 550 by using the coil 542 to induce communication signals onto the existing pacing lead 552. The firmware of the implant 550 is reprogrammed to detect these communication signals (which arrive via an electric signal sensing input of the pacemaker) as described below.

The interface between the internal controller 535 and the coil 542 is implemented by a coil driver 540. The coil driver 540 may be implemented using a FET or any of a variety of alternative approaches, the implementation of which will be apparent to persons skilled in the relevant arts.

After all these components 530, 542 have been implanted into the patient's body, an external ultrasound controller 520 that remains outside of the patient's body can communicate with the additional implanted components 530 by sending ultrasound signals to the additional implanted components 530. Communication between the external controller 525 in the external unit 520 and the internal controller 535 in the additional implanted components 530 is similar to the communication described above in connection with the corresponding components in FIG. 1. But the communication between the internal controller 535 and the implant 550 differs in that the FIG. 5 embodiment relies on the EM coil 542 (instead of a hardwired connection, as in FIG. 1).

The FIG. 5 embodiment relies on the establishment of a second communication link that uses ultrasound signals to control the implant 550. As described above in connection with FIG. 1, relying on an ultrasound communication link provides a high degree of immunity to interference and hacking because ultrasound signals above 100 kHz cannot pass through air gaps. As a result, in order to communicate with the implant 550, direct contact between the external ultrasound controller 520 (which includes an ultrasound transducer) with the wearer's body must be established. The difficulty of establishing direct contact without the user's knowledge provides a high degree of additional security.

Retrofitting of the conventional implant 550 (e.g., a pacemaker) in the FIG. 5 embodiment may be implemented using the following four modifications: (a) an electromagnetic coil 542 is positioned around the leads that are ordinarily used by the pacemaker to stimulate the heart and monitor the cardiac electric activity; (b) the additional implanted components 530 is implanted near the pacemaker leads, with the output of the coil driver 540 connected to the coil 542. The internal controller 535 is controlled by ultrasound signals as described above in connection with FIG. 1. An output from the internal controller 535 interfaces with the coil driver 540, which drives the electromagnetic coil 542 to generate electric currents in the coil; (c) the software (e.g., firmware) of the implant 550 is modified to enable a new mode of communication based on detection of the electrical signals that have been induced in the lead 552 by the additional implanted components 530 (via the EM coil 542); and (d) the software (e.g., firmware) of the implant 550 is modified to completely disable RF communication. The software/firmware updates for implementing modifications (c) and (d) are described in greater detail below.

The additional implanted components 530 and the EM coil 542 may be configured so that they induce signals with amplitudes that resemble those of ECG, i.e, in the mV range (e.g., less than 5 mV) and apply those signals to the lead 552. Preferably, the shape characteristics of these signals are clearly distinct from the cardiac electric signals that are ordinarily sensed by the implant 550. This may be accomplished, for example, using a series of short pulses or relatively high frequencies (e.g., in the 1 kHz to 100 kHz range) to ensure that these communication signals are not misinterpreted by the pacemaker as cardiac activity signals.

In this FIG. 5 embodiment, the signals generated by the electromagnetic coil 542 are of sufficient amplitude so that they can be detected despite the fact that the lead 552 is typically shielded. For example, if the shielding provides an attenuation of 1000×, a 0.5V signal outside the shield will translate to a 0.5 mV signal inside the shield, which will appear at the input to the pacemaker 550. But because conventional pacemakers are designed to detect signals with amplitudes less than 1 mV, the communication signal arriving at the pacemaker's lead 552 will be large enough for the pacemaker 550 to detect. Note, however, that in situations where the shielding around the lead 552 of the pacemaker is robust enough to prevent signals from the coil 542 from being coupled onto the lead 552 at levels that can be detected by the pacemaker 550, an alternative approach for coupling signals onto the pacemaker's lead (e.g., the one described below in connection with FIG. 10) should be used in place of the configuration depicted in FIG. 5.

Data may be encoded onto the signals that are coupled onto the lead 552 of the pacemaker 550 using any of a variety of encoding approaches that will be apparent to persons skilled in the relevant arts. Examples include frequency and/or time intervals/durations based approaches, digital modulation/demodulation techniques (including but not limited to amplitude-shift keying, phase-shift keying, pulse-position modulation, etc.) and analog modulation/demodulation techniques (including but not limited to amplitude modulation, frequency modulation, phase modulation, etc.) etc. The information carried by these signals can include, among others, the same information that is normally provided by the RF input in conventional implants. Examples include control of the stimulating pulse amplitude and rate, interval between the various stimuli applied to different cardiac chambers, etc.

Modification (c) enables the implant 550 to detect the signals that have been imposed by the coil 542 onto the lead 552 of the pacemaker 550 and extract the data that was embedded in those signals. Of course, the extraction of the data from the signals that arrive at the input of the pacemaker 550 will depend on the approach that was used to encode the data into the signals by the internal controller 535.

Figure 6A:
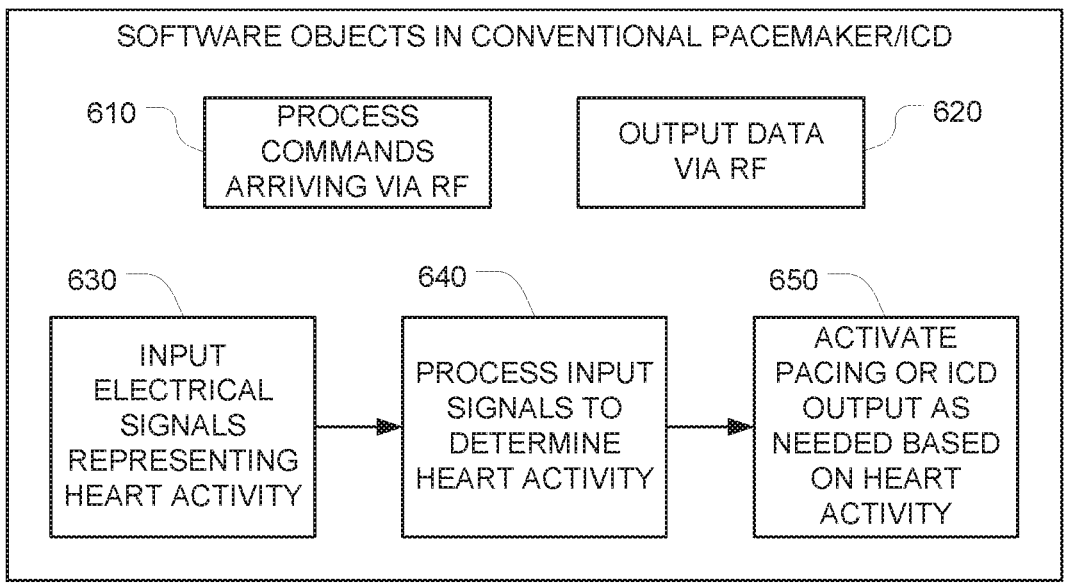
FIG. 6A is a block diagram of software objects that are implemented in a conventional pacemaker or ICD.

FIG. 6A is a block diagram of software objects that are implemented in a conventional pacemaker or ICD. It includes a software object 610 for processing commands that arrive at the pacemaker via RF, and a software object 620 for outputting data from the pacemaker to the external world via RF. It also includes a software object 630 for inputting electrical signals that represent heart activity. (Those electrical signals arrive at the pacemaker's input connector via the pacemaker's lead.) Those input signals are processed in software object 640 to determine heart activity. The output from this software object 640 is provided to software object 650, which activates a pacing output or an ICD output as needed when a significant irregularity in the heart activity (as determined by software object 640) is detected.

Figure 6B:
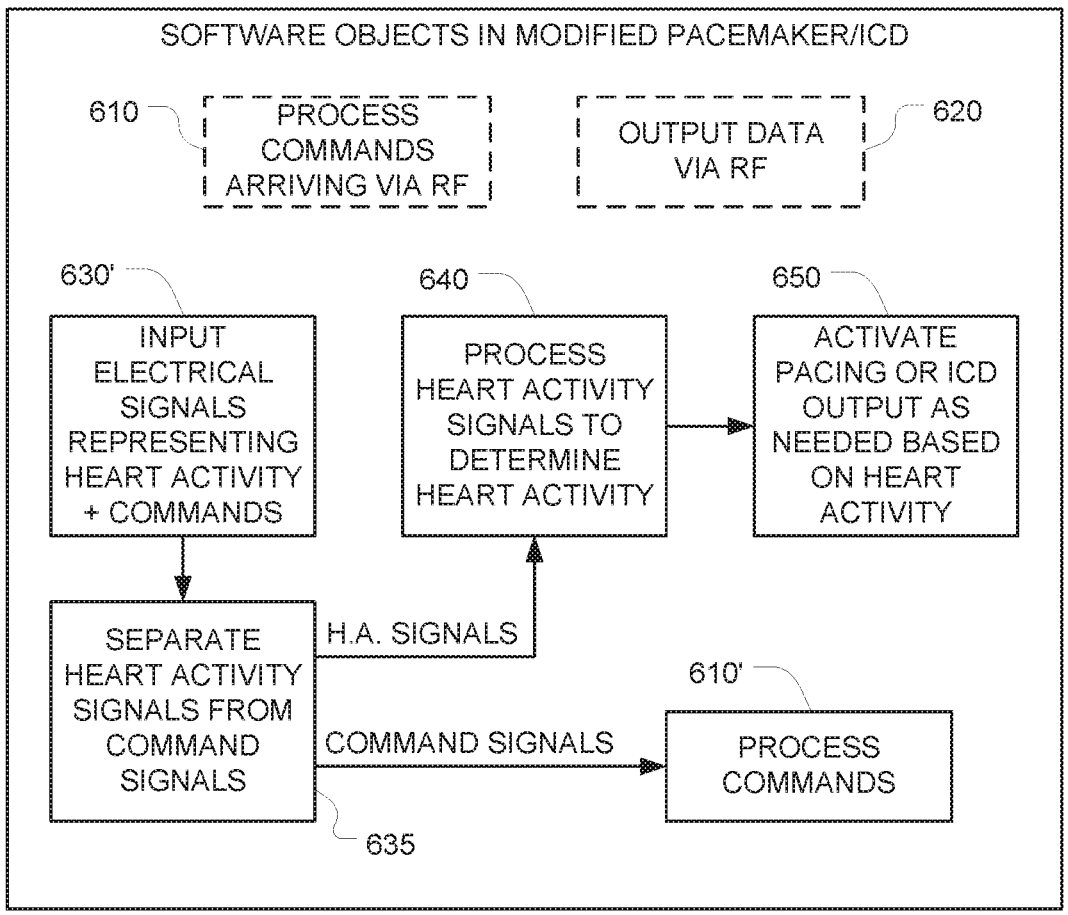
FIG. 6B is a block diagram of software objects that are included in the modified pacemaker depicted in FIG. 5.

FIG. 6B is a block diagram of the software objects 610', 630', and 635-650 that are included in the modified pacemaker 550 depicted in FIG. 5 which has been modified by modification (c). Software object 630' inputs electrical signals that represent both heart activity and commands. The former originate from the heart, and the latter originate from the coil 542 that has been positioned in proximity to the pacemaker's lead 552. But both arrive at the pacemaker's input pacemaker's lead 552. Detection of the signals arriving at the pacemaker's input in software object 630' is similar to the detection implemented in software object 630 in FIG. 6A. But instead of forwarding all of the detected signals to software object 640 (as in FIG. 6A), the FIG. 6B embodiment includes an additional software object 635 that separates the heart activity signals from the command signals, and forwards each of those categories of signals to a different destination for processing.

One approach for implementing this software object 635 is by using a digital filter. More specifically, heart activity electrical signals will always be limited to a particular frequency band. The command signals that are coupled onto the pacemaker's lead 552 are preferably configured so that all of their power lies above this particular frequency band. As a result, the software object 635 can separate the heart activity signals from the command signals based on their frequency content. More specifically, the low frequency signals will be recognized as heart activity signals and forwarded to software object 640 for processing; and the high-frequency signals will be recognized as command signals and forwarded to the software object 610' for processing. Software objects 640/650 in this embodiment operate in the same way as the corresponding software objects 640/650 in FIG. 6A. And software object 610' in this embodiment is designed to process commands in a manner that corresponds to the processing of commands by software object 610 in FIG. 6A, except that the commands will now be arriving from a different source i.e., the output of the "separation" object 635.)

Modification (d) is the software-initiated disabling of RF communication. Note that many conventional pacemakers already include a built-in hardware safety mechanism designed to disconnect the RF input from the implant control before cardiac defibrillation is attempted. Emergency personnel use a special RF signal transmitter to activate this safety mechanism. For these devices, modification (d) can be implemented by activating this built in safety mechanism to disconnect the RF input, which will prevent all RF communications from reaching the implant 550, thereby rendering the implant 550 immune from any attempts to control it via RF signals. Alternatively, modification (d) may be implemented completely in software by configuring the updated software so that the software object 610 and 620 (shown in dashed lines in FIG. 6B) are permanently disabled. This may be accomplished, for example, by deactivating software/firmware routines that interface with the RF transceiver. As a result of either of these modifications, the modified pacemaker 550 will no longer be able to process commands that arrive via RE or output data to the external world via RF.

Note that the software/firmware updates (c) and (d) described herein are implemented as a one-time initial set up using the conventional RF communication mode. After this initial set up has been completed, any subsequent attempt to initiate communication with the implant 550 via RE alone will no longer work.

Once these four modifications (a)-(d) have been made, communication with the internal controller 535 can only be established by placing the external unit 520 in contact with the user's skin (e.g., on the user's chest), and using external unit 520 to send ultrasound signals to the additional implanted components 530 as described above in connection with FIG. 1. The additional implanted components 530 will then relay the communication received from the external unit 520 to the implant 550 by generating appropriate signals using the EM coil 542. Those signals are picked up by the lead 552, and the updated software in the implant 550 recognizes those signals as communication signals.

Because all RF communications have been completely disabled in this embodiment. Operation of this embodiment is similar to the operation described above in connection with FIG. 1 in that the implant 550 cannot be controlled by RF, and ultrasound signals become the only way to control the implant 550. However, instead of using a hardwired input to control the implant (as in FIG. 1), this FIG. 5 embodiment uses using the newly established communication path that relies on the ECG input (i..e., the lead 552) of the implant 550 to convey the control signals into the implant 550.

Figure 7:
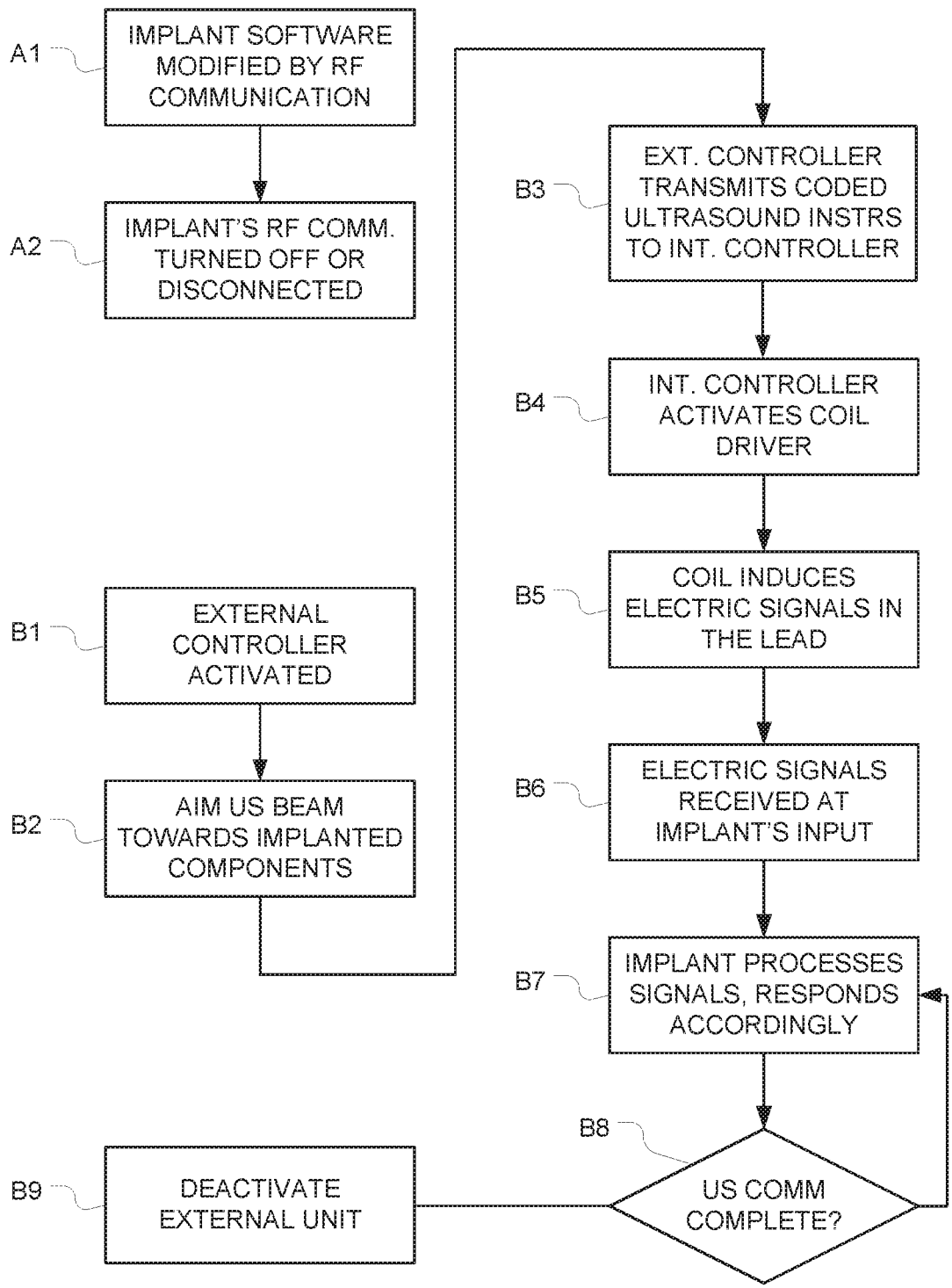
FIG. 7 is a flowchart that depicts one suitable approach for implementing communication with the implant in the FIG. 5 embodiment.

FIG. 7 is a flowchart that depicts one suitable approach for implementing communication with the implant in the FIG. 5 embodiment. Steps A1 and A2 are the steps for implementing a one-time initial set up, in which the implant software is modified by RF communication, and the implant RF communication is turned off or disconnected. After this initial set up has been completed, steps B1-B9 can be used to communicate with the implant 550. In step B1, the external controller 525 in the external unit 520 is activated. In step B2, an ultrasound beam is aimed from the ultrasound transducer 42 in the external unit 520 to the ultrasound transducer 52 in the additional implanted components 530. In step B3, the external controller 525 transmits coded ultrasound instructions to the internal controller 535. In step B4, the internal controller 535 activates the coil driver 540; and in step B5, the coil 542 induces electric signals in the lead 552 of the implant 550. In step B6, electric signals are received at the input of the implant 550. In step B7, the implant 550 processes the signals that arrive at its lead as a command, and respond to that command accordingly. Note that during step B7, the external unit 520 can communicate with the implant 550 and send control sequences to the implant by sending ultrasound signals to the additional implanted components 530 which in turn drives the EM coil 542 so that the appropriate signals will be received by the implant 550. Step B8 is a test for the end of the ultrasound communication session. If the session is not over, the system returns to step B7 for additional input. If the session is over, the external unit is deactivated in step B9.

Although not depicted in FIG. 5, components that correspond to item 60-70 in FIG. 2 may optionally be added to the FIG. 5 embodiment, to add the same "echo back" functionality provided by those components in the context of FIG. 2 (as described above)

Figure 8:
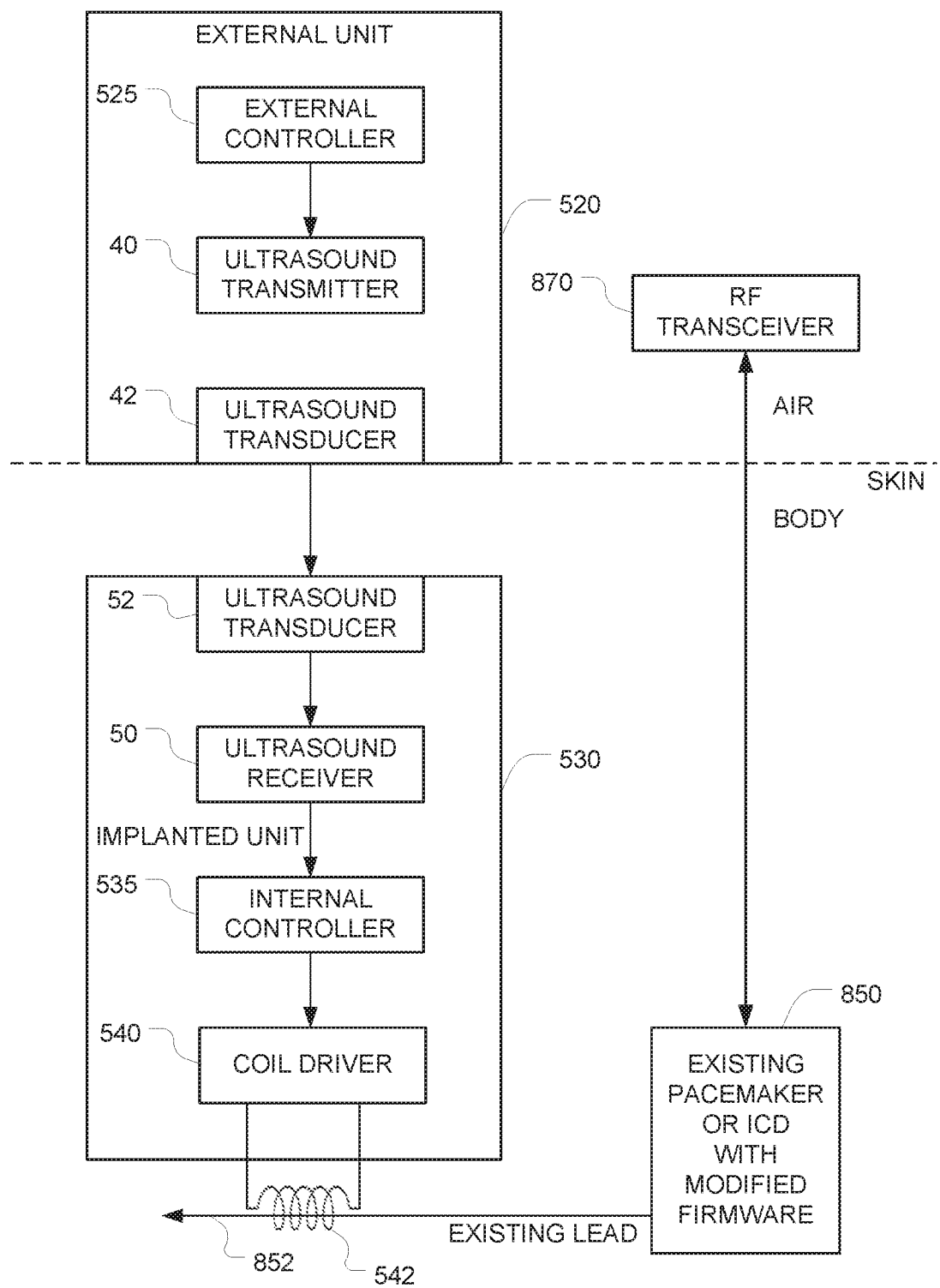
FIG. 8 is a schematic diagram of another system that retrofits protection to a previously implanted implant.

FIG. 8 is a schematic diagram of another system that overcomes the disadvantages of the prior art by retrofitting protection to a previously implanted implant. Similar to the FIG. 4 embodiment described above, this FIG. 8 embodiment includes two communication channels from the outside world to the implant 850. The first is the RF channel between the RF transceiver 870 outside the body and an RF interface implanted inside the body (i.e., within the implant 850 itself). The second is the ultrasound channel between the ultrasound transducer 42 outside the body and the ultrasound transducer 52 implanted inside the body. Note that these ultrasound transducers 42, 52 in FIG. 8 are parts of the external unit 520 and the additional implanted components 530, respectively, described above in connection with FIG. 5. In some variants of the FIG. 8 embodiment, an ultrasound handshake between the ultrasound transducers 42, 52 is required before communication between the RF interface 850, 870 is enabled.

This embodiment is similar to the FIG. 5 embodiment in that the same modifications (a), (b), and (c) described above in connection with FIG. 5 are also made in this FIG. 8 embodiment. The main distinction between the FIG. 8 embodiment and the FIG. 5 embodiment is that instead of modifying the software/firmware of the implant to completely disable RF communication using modification (d) described above in connection with FIG. 5, a different modification to the software/firmware is made in this FIG. 8 embodiment. More specifically, this FIG. 8 embodiment replaces modification (d) with modification (e), which dynamically disables RF communication. Once this modification (e) has been made, the RF communication capability can be either enabled or disabled in software.

After modification (e) is implemented in the FIG. 8 embodiment, the software of the implant 850 will ordinarily ignore all communications arriving via RF unless and until an authorized enable signal arrives via the ultrasound communication channel. Once an authorized enable signal arrives via ultrasound, the software activates the RF communication capability, and communication can proceed in a manner similar to RF communication with conventional implanted devices. In this regard, the operation of this FIG. 8 embodiment is similar to the operation of the FIG. 4 embodiment described above, and the discussion of how ultrasound signals can be used to enable or disable the RF communication in the FIG. 4 embodiment applies to this FIG. 8 embodiment. The main difference is that instead of coupling the control signals from the additional implanted components 430 into the implanted device 450 via a hardwired input (as in FIG. 4), the control signals from the additional implanted components 530 in this FIG. 8 embodiment are coupled into the implant 850 using the same inductive-coupled interface between the coil 542 and the lead of the pacemaker described above in connection with FIG. 5.

In these embodiments, the system may optionally be programmed to automatically disable RF communication in software after a certain amount of time (e.g. 30 seconds from the start of the communication session) has elapsed. Alternatively, the system may be programmed to disable RF communication in software upon receipt of a disable signal that arrives via either the ultrasound channel or via the RF channel itself.

Figure 9:
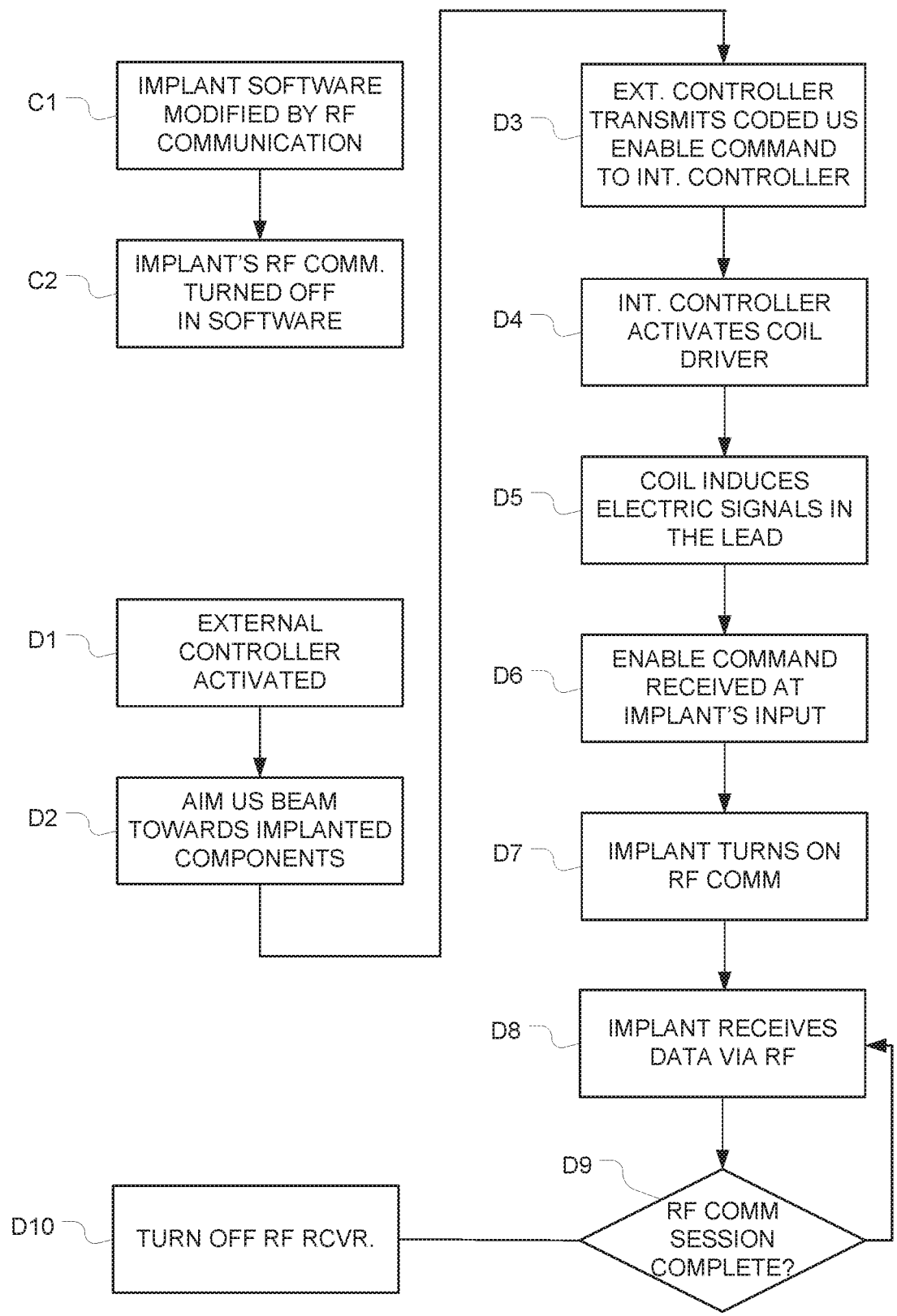
FIG. 9 is a flowchart that depicts communication with the implant in the FIG. 8 embodiment.

FIG. 9 is a flowchart that depicts communication with the implant in the FIG. 8 embodiment (in which RF communication can be temporarily enabled in response to an activation signal or signals received via ultrasound). Steps C1 and C2 are the steps for implementing a one-time initial set up, in which the implant software is modified by RF communication, and the implant RF communication is turned off in software. After this initial set up has been completed, steps D1-D10 can be used to communicate with the implant. In step D1, the external controller 525 in the external unit 520 is activated. In step D2, an ultrasound beam is aimed from the ultrasound transducer 42 in the external unit 520 to the ultrasound transducer 52 in the additional implanted components 530. In step D3, the external controller 525 transmits a coded ultrasound enable instruction to the internal controller 535. In step D4, the internal controller 535 activates the coil driver 540; and in step D5, the coil 542 induces electric signals in the lead 852 of the implant 850. In step D6, electric signals that correspond to an enable command are received at the input of the implant 850. In step D7, the implant 850 turns on its RF communication ability in response to the enable command.

In step D8, the implant receives data via RF. Note that during step D8, the external world can communicate with the implant 850 and send control sequences to the implant via the conventional RF communication path, just like in conventional pacemakers. Step D9 is a test for the end of the RF communication session. Examples of events that can end an RF communication session include a timeout (e.g., one minute after initiation of RF communication), receipt of a disable command via RF, and receipt of a disable command that was transmitted into the body via ultrasound and arrived at the implant 850 via the lead 852. If the session is not over, the system returns to step D8 for additional input. If the session is over, the RF unit in the implant 850 is deactivated or inhibited in step D10. After execution of step D10, the RF communication path is disabled, and the external world can no longer communicate with the implant 850 via the RF path. Notably, the ultrasound signals are used in these embodiments to either enable or disable the standard RF communication. The use of ultrasound as a prerequisite to enabling RF communication provides enhanced security even though a portion of the communication is implemented via RF. This is because the vast majority of the time, the implant is not "listening" for RF communication.

Optionally, these embodiments may implement a handshake procedure ultrasound to enable or disable the RF communications. The handshake may be designed to require an approved Programmer—IMC communication session as a prerequisite for the continued use of the RF communication channel.

Note that in alternative embodiments (not shown) the RF transceiver 870 in FIG. 8 may be replaced by an RF receiver, and the software/firmware in the pacemaker 850 may be programmed to permanently disable RF reception. RF transmission, on the other hand can be selectively enabled or disabled by commands received via the ultrasound channel. Operation of these embodiments will then be similar to the operation of FIG. 3, discussed above, except that the interface with the existing pacemaker is accomplished by inductively coupling signals onto the pacemaker's lead (instead of via signals that are applied to the pacemaker a hardwired input, as it is in FIG. 3).

Most conventional pacemakers have an associated lead, one end of which is affixed to a target location in the patient's heart, while the other end connects to the pacemaker using a connector. This arrangement may be implemented, for example, using a male plug at the proximal end of the lead that plugs into a female connector on the body of the pacemaker. This connector facilitates replacement of the pacemaker by simply unplugging the old pacemaker from the proximal end of the existing lead, and plugging the new pacemaker on to the proximal end of that same lead.

Figure 10:
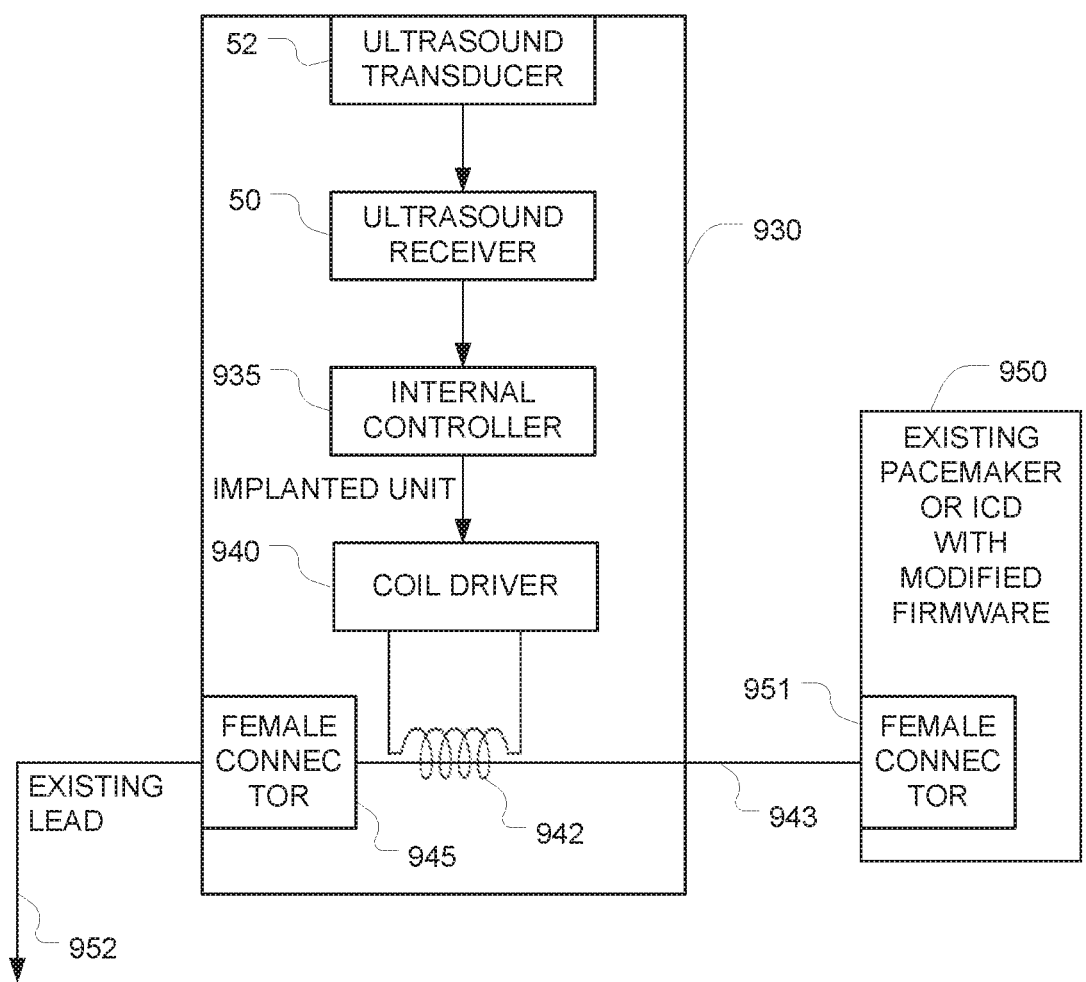
FIG. 10 is a block diagram of an alternative approach for coupling signals onto the analog input of a pacemaker or ICD using a coil.

FIG. 10 takes advantage of this connector to provide an alternative approach for coupling signals onto the analog input of a pacemaker or ICD using a coil. More specifically, we assume that an existing pacemaker 950 has previously been installed in a patient's body, with the proximal end of an existing lead 952 connected to a connector 951 on the existing pacemaker 950. The distal end of the existing lead 952 terminates in the patient's heart. To implement this approach, the existing lead 952 is unplugged from the connector 951 of the existing pacemaker 950 and plugged into the female connector 945 of the additional implanted components 930. This operation interposes the additional implanted components 930 between the existing lead 952 and the existing pacemaker 950. The components 50, 52, 935, 940 in this FIG. 10 embodiment operate in the same way as the corresponding components in the FIGS. 5 and 8 embodiments described above. But in this FIG. 10 approach, instead of wrapping the coil 542 around a shielded portion of the existing lead of the pacemaker((as described above in connection with FIGS. 5 and 8), the coil 942 wraps around the additional length of lead 943 without any intervening shielding. This advantageously provides improved coupling between the coil 942 and the additional length of lead 943, and overcomes the problems caused by the shielding that surrounds the existing lead 552/852 in the FIGS. 5 and 8 embodiments described above. Preferably, shielding is provided on the body of the additional implanted components 530 so that the pacemaker will not be adversely affected by spurious RF. But because the coil 942 and the additional length of lead 943 are both positioned inside this shielding, the shielding does not interfere with the coupling between those two components.

The embodiments described herein provide a safe way to control the activity of the implanted devices from the outside or from another implanted device, for example to alter the heart rate, cardiac stimulation timing, etc. from the outside. Specifically, the system does not allow any interference with the implant function by an unauthorized agent.

In any of the embodiments described herein, the frequency of the ultrasound used for communication is preferably between 0.5-20 MHz, and more preferably between 1-5 MHz or between 1-3 MHz. In some preferred embodiments, ultrasound with a frequency of around 2 MHz is used. These frequency ranges are preferred because low frequency ultrasound (e.g. 20-100 kHz) can cross the air/body interface with relatively low losses, and therefore may not provide the desired level of security. In contrast, the corresponding losses for higher frequency ultrasound (e.g. on the order of 1-5 MHz) are large enough to provide the desired level of security. As for the upper limit, the frequency of the ultrasound is preferably below 10 MHz, because higher frequencies will undergo significant attenuation as they pass through tissue in the body, to the point where the signal may not be able to reach the implant.

The ultrasound power is preferably within the allowed range, preferably less than one tenth the maximal allowed power. The depth of penetration of 2 MHz signals is sufficient for any intra-body location. The ultrasound beam generated should preferably be relatively wide such that there is no need to point the beam axis exactly at the implant. Examples of suitable transducers include single element, small diameter (2-10 mm) Piezo electric elements. The transducer's contact with the subject's skin is preferably mediated by conventional ultrasound gel. The transducer can be hand held or can have a patch like structure and he attached to the skin by an adhesive like an ECG electrode.

Finally, the invention is not limited to the contexts of pacemakers and ICDs described above. To the contrary, it may be used in the contexts of a wide variety of alternative implantable devices that have analog inputs.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An implantable apparatus comprising:
   an implantable device configured for implantation into a body, the implantable device having an RF transceiver and a first input configured to detect analog electrical signals, wherein the implantable device has been modified by a software update from an original state in which the implantable device is configured to accept control commands that arrive via the RF transceiver to an updated state in which the implantable device is configured to accept control commands that arrive via the first input and ignore control commands that arrive via the RF transceiver;
   a coil that is inductively coupled with a lead connected to the first input of the implantable device;
   a coil driver circuit configured to energize the coil in response to application of control signals;
   a first ultrasound transducer that generates a first electrical output signal in response to a first incoming ultrasound signal;
   a first ultrasound frequency receiver that generates, based on the first electrical output signal, first data corresponding to commands that have been encoded onto the first incoming ultrasound signal; and
   a first controller configured to generate the control signals based on the first data, wherein the control signals are routed to the coil driver circuit,
   wherein the control signals generated by the first controller are configured to cause the coil driver circuit to energize the coil so as to induce, onto the lead, analog signals that correspond to the control commands that arrive via the first input of the implantable device.

2. The implantable apparatus of claim 1 wherein, in the updated state, the implantable device is configured to keep the RF transceiver disabled at all times.

3. The implantable apparatus of claim 2, wherein the implantable device is configured to keep the RF transceiver disabled at all times by activating hardware that disconnects an RF input of the implantable device.

4. The implantable apparatus of claim 2, wherein the implantable device is configured to keep the RF transceiver disabled at all times by deactivating software routines that interface with the RF transceiver.

5. The implantable apparatus of claim 1 wherein, in the updated state, the implantable device is configured to temporarily enable the RF transceiver in response to a first specific control command that arrives via the first input, and to keep the RF transceiver disabled at all other times.

6. The implantable apparatus of claim 5, wherein the implantable device is configured to terminate the temporary enablement of the RF transceiver in response to a second specific control command.

7. The implantable apparatus of claim 5, wherein the implantable device is configured to terminate the temporary enablement of the RF transceiver automatically after a period of time has elapsed.

8. The implantable apparatus of claim 1, wherein the implantable device comprises a pacemaker, and wherein the control commands that arrive via the first input control the pacemaker.

9. The implantable apparatus of claim 1, wherein the implantable device comprises an implantable cardioverter defibrillator, and wherein the control commands that arrive via the first input control the implantable cardioverter defibrillator.

10. The implantable apparatus of claim 1, wherein the analog electrical signals have an amplitude of less than 5 mV.

11. A system for implementing secure communication with an implanted device, the system comprising:
    an implantable apparatus including
      the implantable device configured for implantation into a body, the implantable device having an RF transceiver and a first input configured to detect analog electrical signals, wherein the implantable device has been modified by a software update from an original state in which the implantable device is configured to accept control commands that arrive via the RF transceiver to an updated state in which the implantable device is configured to accept control commands that arrive via the first input and ignore control commands that arrive via the RF transceiver,
      a coil that is inductively coupled with a lead connected to the first input of the implantable device,
      a coil driver circuit configured to energize the coil in response to application of control signals,
      a first ultrasound transducer that generates a first electrical output signal in response to a first incoming ultrasound signal,
      a first ultrasound frequency receiver that generates, based on the first electrical output signal, first data corresponding to commands that have been encoded onto the first incoming ultrasound signal, and
      a first controller configured to generate the control signals based on the first data, wherein the control signals are routed to the coil driver circuit,
    wherein the control signals generated by the first controller are configured to cause the coil driver circuit to energize the coil so as to induce, onto the lead, analog signals that correspond to the control commands that arrive via the first input of the implantable device; and an auxiliary apparatus including
- a second controller configured to generate commands for controlling the implantable device,
- a first ultrasound frequency transmitter that encodes the commands generated by the second controller onto a first driving signal, and
- a second ultrasound transducer that generates a second ultrasound output signal in response to the first driving signal.

12. A method of retrofitting an implantable device to provide secure communications, the method comprising:

obtaining the implantable device configured for implantation into a body, the implantable device having an RF transceiver and a first input configured to detect analog electrical signals, wherein the implantable device is configured to accept control commands that arrive via the RF transceiver;

modifying software of the implantable device to an updated state in which the implantable device is configured to accept control commands that arrive via the first input and ignore control commands that arrive via the RF transceiver;

inductively coupling a coil to a lead connected to the first input of the implantable device;

energizing the coil in response to application of control signals;

generating a first electrical output signal in response to a first incoming ultrasound signal;

generating, based on the first electrical output signal, first data corresponding to commands that have been encoded onto the first incoming ultrasound signal; and generating the control signals based on the first data, wherein the control signals are configured to energize the coil so as to induce, onto the lead, analog signals that correspond to the control commands that arrive via the first input of the implantable device.

13. The method of claim 12 wherein, in the updated state, the implantable device is configured to keep the RF transceiver disabled at all times.

14. The method of claim 13, wherein the implantable device is configured to keep the RF transceiver disabled at all times by activating hardware that disconnects an RF input of the implantable device.

15. The method of claim 13, wherein the implantable device is configured to keep the RF transceiver disabled at all times by deactivating software routines that interface with the RF transceiver.

16. The method of claim 12 wherein, in the updated state, the implantable device is configured to temporarily enable the RF transceiver in response to a first specific control command that arrives via the first input, and to keep the RF transceiver disabled at all other times.

17. The method of claim 16, wherein the implantable device is configured to terminate the temporary enablement of the RF transceiver in response to a second specific control command.

18. The method of claim 16, wherein the implantable device is configured to terminate the temporary enablement of the RF transceiver automatically after a period of time has elapsed.

19. The method of claim 12, wherein the implantable device comprises a pacemaker, and wherein the control commands that arrive via the first input control the pacemaker.

20. The method of claim 12, wherein the implantable device comprises an implantable cardioverter defibrillator, and wherein the control commands that arrive via the first input control the implantable cardioverter defibrillator.

* * * * *